United States Patent [19]

Nakamura

[11] 4,214,973
[45] Jul. 29, 1980

[54] BLOOD SERUM APPLICATOR FOR USE IN CATAPHORETIC APPARATUS

[75] Inventor: Kazuhiko Nakamura, Hachioji, Japan

[73] Assignee: Olympus Optical Co., Ltd., Tokyo, Japan

[21] Appl. No.: 963,324

[22] Filed: Nov. 24, 1978

[30] Foreign Application Priority Data

Dec. 15, 1977 [JP] Japan .................. 52-167689[U]

[51] Int. Cl.² ............................................ G01N 27/28
[52] U.S. Cl. ............... 204/299 R; 204/180 G;299 R; 204/180 S; 73/61.1 C
[58] Field of Search ........... 204/180 R, 180 S, 180 G, 204/299 R; 73/61.1 R, 61.1 C; 239/172, 303

[56] References Cited

U.S. PATENT DOCUMENTS

| | | | |
|---|---|---|---|
| 3,505,858 | 4/1970 | Kohn | 73/61.1 |
| 3,616,387 | 10/1971 | Siebert et al. | 204/180 G |
| 3,839,183 | 10/1974 | Klein et al. | 204/299 |
| 3,930,973 | 1/1976 | Nerenberg | 204/180 S |

Primary Examiner—Arthur C. Prescott
Attorney, Agent, or Firm—Ostrolenk, Faber, Gerb & Soffen

[57] ABSTRACT

The serum application for use in a cataphoretic apparatus comprises a penpoint which is mounted on the lower end of a plate-shaped penpoint support member, the upper end of which is formed with a hook to permit the support member to be suspended from a support arm to maintain the serum applying surface of the penpoint in parallel relationship with the surface of a serum bearing member. The upper end face of a support arm which is engaged by the hook is formed to lie in a plane parallel to the surface of the serum bearing member. The penpoint support member is vertically slidable relative to the vertical major surface of the support arm by providing a guide pin and guide slot arrangement.

9 Claims, 8 Drawing Figures

BLOOD SERUM APPLICATOR FOR USE IN CATAPHORETIC APPARATUS

BACKGROUND OF THE INVENTION

The invention relates to a blood serum applicator for use in cataphoretic apparatus, and more particularly, to such applicator which may be used to apply a sample of blood serum to a serum bearing member.

As is well recognized, an automatic cataphoretic apparatus is arranged to perform the supply of a serum bearing member, the application of a serum thereto, a cataphoretic process, the steps of dyeing, decolorizing and drying, photometry and recording in a sequential and automatic manner (see pending U.S. patent application Ser. No. 829,957 and German patent application No. P 27 40 073.3). Specifically, a roller which wets a serum bearing member with a buffer solution feeds it into a serum application station where a blood serum to be examined is applied to the bearing member, which is then supplied into a cataphoresis vessel. A cataphoretic process takes place within the vessel, and after the completion of the cataphoretic process, the bearing member is transferred into a dyeing vessel where the steps of dyeing, decolorizing and drying take place. The dried bearing member is subject to photometry with a densitometer. The data obtained by the photometry is recorded by means of a recorder.

A blood serum bearing member comprises a sheet of cellulose acetate to which blood serum is applied with a penpoint application in a rectilinear form of a given narrow width. The serum is then electrically energized to obtain a fractionated pattern of the serum.

A conventional serum application is illustrated in FIGS. 1 and 2. Referring to these Figures, the serum applicator comprises a plurality of serum application members 3 which are carried by a support arm 4 in juxtaposition. The member 3 includes a plate-shaped penpoint 1 having an applying surface 1a which is attached to a support shank 2. The support shank 2 fixedly carries a pin 5 which is fitted in a slot 4a formed in the support arm 4, thereby allowing a limited vertical movement of the penpoint as permitted by the vertical extent of the slot. In use, the support arm 4 is lowered to immerse the penpoint 1 of the individual application members 3 into a supply of blood serum. After the serum is applied to the surface 1a of the penpoints, the support arm 4 is raised and moved to a location over a blood serum bearing member 6 where it is lowered to move the application members 3 down so that the surfaces 1a may be brought into contact with the bearing member 6, thus applying the serum to the latter.

However, the described construction of the serum application results in a disadvantage that the serum is deposited on the bearing member in a deformed form, as illustrated in FIGS. 3(C) and (D). Specifically, the support arm 4 is channel-shaped so as to have a pair of limbs 4d, 4e which are formed with openings 4b, 4c extending therethrough for allowing the shank 2 to pass therethrough. It is difficult to achieve a high accuracy in the size and location of openings 4b, 4c. If the vertically spaced openings are misaligned or if there is any clearance between the edge of the openings and the shank 2, the application member 3 will assume a slanted or inclined position. If such an application member is directly used in the application of the blood serum to the bearing member, the surface 1a of the penpoint 1 will be inclined when abutting against the bearing member 6, as illustrated in FIGS. 3(A) and (B). As a consequence, the deposition of serum 20 will be offset to one side, as illustrated in FIGS. 3(C) and (D). Another difficulty is that of achieving a high accuracy in the manufacturing of the pin 5 and its engagement with the slot 4a. If the pin 5 extends in a wrong direction or if there is a clearance between the pin and the slot 4a, the applying surfaces 1a of the individual pin point 1 will not be aligned with each other on the bearing member 6 but will be staggered thereon, with the result that the applied samples of serum will be similarly staggered when they are subject to a cataphoretic process, which is undesirable.

SUMMARY OF THE INVENTION

It is an object of the invention to provide a blood serum applicator for use in cataphoretic apparatus which eliminates the above disadvantages of the conventional serum applicator, by providing support members which support serum applying penpoints and which are mounted on a support arm in suspended form by their own gravity so that when the support arm is lowered, all of the applying surfaces of the penpoints will be aligned with each other on a serum bearing member when they are disposed in abutment against the latter.

In accordance with the invention, a support arm in the form of a horizontally elongate plate-shaped member has an upper end face which is parallel to the surface of a blood serum bearing member. A penpoint support member has a hook which is suspended from the upper end face of the support arm so that the applying surface of a penpoint is maintained parallel to the surface of the bearing member. When the support arm is lowered, the applying surfaces are entirely and uniformly in abutment against the surface of the bearing member. In this manner, it is assured that the blood serum be applied to the bearing member precisely in a recilinear form of a given, narrow width. This is also assisted by forming both the support arm and the support members from plate-shaped members each having a vertical major surface, which are maintained in contact when moving the penpoint support members relative to the support arm in the vertical direction. This prevents an angular movement of the support members. The degree of parallelism between the applying surface of the penpoint and the surface of the serum bearing member depends on the accuracy with which the upper end face of the support arm and the hook surface of the support member are machined. The alignment of the applying surfaces of individual penpoint on the bearing member depends on the accuracy of machining of the mating vertical surfaces of the support arm and support members. However, it will be appreciated that these machining accuracies can be significantly improved inasmuch as the involved machining operation represents a planing.

The penpoint support member is vertically movable with respect to the support arm by a pin and slot arrangement. Specifically, the support member is formed with a vertically elongate guide slot having a lateral width which is slightly greater than the diameter of a guide pin that is integral with a locking screw which is in turn fixedly mounted on the mating vertical surface of the support arm. Consequently, if the applying surface of the penpoint is inclined when it is disposed in abutment against the bearing member, it will angularly move under gravity as the support arm is lowered, thus bringing the entire applying surface of the penpoint into abutment against the surface of the bearing member.

DESCRIPTION OF THE PREFERRED EMBODIMENT

Figure 1:
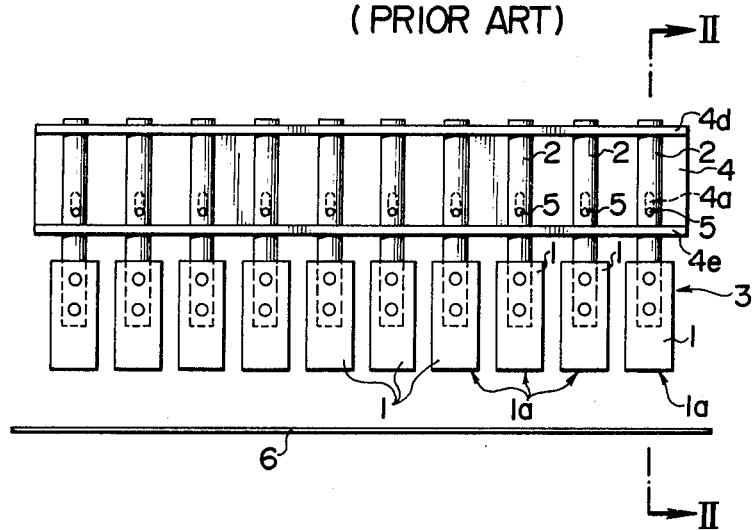
FIG. 1 is a front view showing a conventional serum applicator.
Figure 2:
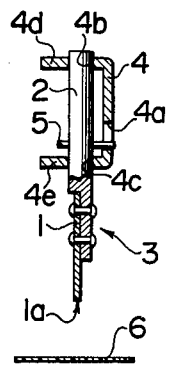
FIG. 2 is a cross-section taken along the line II—II shown in FIG. 1.
Figure 3A:
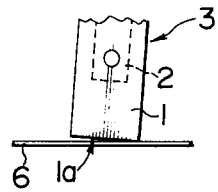
FIGS. 3(A) to (D) are front views of part of the applicator when the applying surface assumes an inclined position relative to the surface of the bearing member, and plan views of the resulting deposition of the blood serum.
Figure 3B:
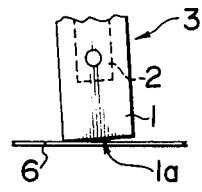
Figure 3C:
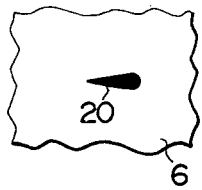
Figure 3D:
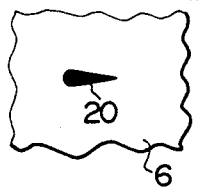
Figure 4:
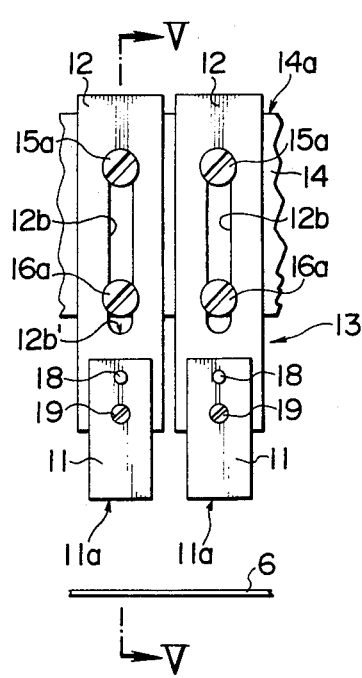
FIG. 4 is a fragmentary, enlarged front view of the serum applicator according to one embodiment of the invention.
Figure 5:
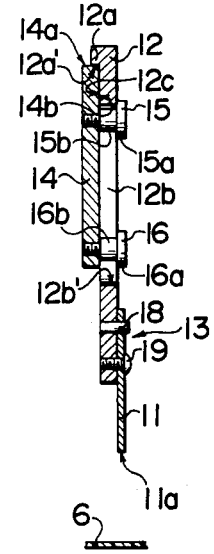
FIG. 5 is a cross-section taken along the line V—V shown in FIG. 4.

Referring to FIGS. 4 and 5, there is shown a penpoint 11 whicn is in the form of a thin, elongate plate member as in the conventional arrangement. The lower end face of the penpoint defines a serum applying surface 11a which is finished to a plane surface for abutment against the surface of a serum bearing member 6. The top of the penpoint 11 is secured to the lower end of a penpoint support member 12 by means of a positioning pin 18 and a locking screw 19. The support member 12 is in the form of a relatively elongate strip. The combination of the support member 12 and the penpoint 11 together constitute a serum application member 13.

The upper end of the support member 12 is formed with a hook 12a which permits the support member 12 to be suspended from a support arm 14 so as to align the applying surface 11a parallel to the surface of the bearing member 6. The hook 12a is formed as a lateral extension which is formed at right angles to the upper end of the support member 12, and has a lower surface 12a' which is adapted to be abutted against the upper end face 14a of the support arm 14. The support member 12 is centrally formed with a vertically elongate guide slot 12b which cooperates with locking screws 15, 16 mounted on the support arm 14 for allowing a vertical movement thereof.

The support arm 14 is formed by a plate member which is elongate in the horizontal direction, and is disposed to present vertical major surfaces. The upper end face as well as the both major surfaces of the support arm 14 are machined to be perpendicular and parallel to the surface of the bearing member 6, respectively. It is to be noted that the support arm 14 is disposed to be movable relative to the bearing member 6.

The hook 12a is engaged with the upper end face 14a of the support arm 14, by engaging the surfaces 12a', 14a. The rear major surface 12c of the support member 12 is disposed in abutment against the front major surface 14b of the support arm 14. Then the support member 12 is suspended from the support arm 14 by gravity. Under this condition, a pair of vertically spaced locking screws 15, 16 are inserted into the guide slot 12b, and then threadably engaged with the support arm 14. The screws 15, 16 have disc-shaped heads 15a, 16a which bear against the edges of the guide slot 12b, thus preventing the support member 12 from being disengaged from the support arm 14. In this manner, the support member 12 is capable of sliding vertically relative to the front wall surface of the support arm 14.

Part of the locking screws 15, 16 define guide pins 15b, 16b, respectively. By way of example, the clearance between pins 15b, 16b and the edge of the guide slot 12b may be approximately 0.3 mm. Thus, the slot 12b has a lateral width which is slightly greater than the diameter of the guide pins 15b, 16b. The provision of such clearance permits an angular movement of the penpoint member 12 by gravity as the support member 14 is lowered even if the applying surface 11a of the penpoint assumes an inclined position when it is in abutment against the surface of the bearing member 6, thus assuring that the entire applying surface 11a of the penpoint bears against the surface of the bearing member 6.

The support member 12 is vertically movable between a first position in which the lower surface 12a' of the hook 12a abuts against the upper end face 14a of the support arm 14 and a second position in which the bottom 12b' of the guide slot 12b bears against the guide pin 16b. When it is suspended from the support arm 14, the applying surface 11a of the penpoint 11 is maintained parallel to the surface of the bearing member 6.

In operation, the support arm 14 carrying a plurality of serum application members 13 is initially lowered to immerse the penpoints 11 in a supply of blood serum, thus causing a deposition of the serum on the individual applying surfaces 11a. Subsequently, the support arm 14 is raised and moved to bring the application members 13 over the blood serum bearing member. At this time, the application members 13 are suspended from the support arm 14 by their own gravity so that the applying surfaces 11a are parallel to the surface of the bearing member 6. The support arm 14 is then lowered to cause the abutment of the applying surfaces 11a of the individual penpoints 11 against the bearing member 6. At this time, the individual applying surfaces 11a lie flat against the bearing member 6, so that the serum which is deposited on the applying surfaces 11a migrates onto the bearing member 6 by capillary action, in a rectilinear form of a given, narrow width. It is expected that the applying surfaces 11a of the plurality of the penpoint 11 which are carried by the support arm 14 may be located at varying distances from the surface of the bearing member 6. In this instance, the application member 13 which has its applying surface 11a initially engaged with the bearing member 6 will move upwardly as the support arm 14 continues to move down, and then other application members 13 will have their applying surfaces 11a disposed in abutment against the bearing member 6. When the application of the serum is completed in this manner, the support arm 14 may be raised, whereupon the applying surfaces 11a of all the application members 13 will move away from the surface of the bearing member 6 and will be suspended from the support arm 14 by gravity while their applying surfaces 11a are maintained parallel to the surface of the bearing member 6.

From the foregoing description, it will be appreciated that the invention enables an accurate application of a blood serum in an automatic manner.

The present invention may be embodied in other specific forms without departing from the spirit or essential attributes thereof and, accordingly, reference should be made to the appended claims, rather than to the foregoing specification as indicating the scope of the invention.

What is claimed is:

1. A serum applicator for use in a cataphoretic apparatus, comprising:
  a plurality of penpoints, each of said penpoints comprising a plate member having a generally planar serum applying surface on its lower end;
  a plurality of penpoint support members, each of said support members comprising a plate member having a respective one of said penpoints mounted on its lower end and having a hook formed on its upper end, each of said penpoint support members having a planar side surface;
  a support arm in the form of a plate member having planar side and top surfaces;
  a plurality of coupling means equal in number to the number of penpoints, each of said coupling means for slidably coupling a respective said penpoint support member to said support arm such that said planar side surface of its respective penpoint support member lies adjacent said planar support surface of said support arm and such that said respective penpoint support member is freely slidable with respect to said support arm in a direction perpendicular to said planar top surface of said support arm between an uppermost position and a lowermost position; said hook contacting said top surface of said support arm when said penpoint support member is in said lowermost position and orienting said planar serum applying surface of said penpoint in a plane generally parallel to said top surface of said support arm, each of said coupling means coupling its respective penpoint support member to said support arm in such a manner that its respective penpoint support member is pivotable with respect to said support arm independently of the remaining said penpoint support members, whereby the orientation of said planar serum applying surface of each penpoint may change slightly when said serum applying surface is placed in contact with a serum bearing member.

2. A serum applicator according to claim 1 wherein each of said hooks is formed as a lateral extension which is formed at right angles to said upper end of its respective penpoint support member, each said hook having a lower surface which bears against said top surface of said support arm when its respective penpoint support member is in said lowermost position, thus causing its respective penpoint support member to be suspended from said support arm by gravity, when said top surface of said support arm is placed in a horizontal plane and said support member is not in contact with a serum bearing member.

3. A serum applicator according to claim 1, wherein said applicator includes a serum bearing member support surface for supporting a serum bearing member to which serum is to be applied in a horizontal plane and wherein said plate member defining said support arm is elongated in the horizontal direction and said side surface of said support arm is oriented in a vertical plane.

4. A serum applicator according to claim 1 wherein each of said coupling means comprises an elongated guide slot formed in its respective penpoint support member and a guide pin extending from the side surface of said support arm, said guide slot having a lateral width which is slightly greater than the diameter of said guide pin, said guide pin extending through said slot.

5. A serum applicator according to claim 4, wherein each of said coupling means further includes a second guide pin extending from said side surface of said support arm and extending through said slot, said guide pins being so located that they lie along a line perpendicular to said top surface of said support arm.

6. A serum applicator for use in a cataphoretic apparatus, comprising:
  a support arm having a horizontal top and a vertical side surface;
  a plurality of blood application members suspended from said support arm at spaced horizontal intervals, each of said blood serum application members having a generally planar lower end defining a penpoint adapted to deposit blood serum on a serum bearing member when placed in contact therewith and an upper end defining a hook adapted to engage said horizontal top surface of said support arm; and
  coupling means for slidably coupling said blood application members to said support arm in such a manner that each of said blood application members is freely slidable in the vertical direction with respect to said support arm between an uppermost and a lowermost position, said hook of each of said blood application members mating with said horizontal top surface of said support arm when said blood application members are in said lowermost position and orienting said planar lower end in a generally horizontal plane, said coupling means coupling said blood application members to said support arm in such a manner that said blood application members are each independently pivotable with respect to said vertical side surface of said support arm whereby the orientation of said planar lower end of each of said blood application members may change independently of the remaining blood application members, when said planar lower end is placed in contact with a serum bearing member.

7. A serum applicator, comprising:
(A) first and second blood serum applicators each having a planar serum applying surface;
(B) a support arm;
(C) means for coupling said applicators to said support arm in such a manner that:
  (1) said planar serum applying surfaces all lie along substantially the same plane when said serum applying surfaces are not in contact with a serum bearing member;
  (2) each of said applicators are independently slidable with respect to said support arm along a direction lying perpendicular to said same plane; and
  (3) each of said applicators are independently pivotably in a plane perpendicular to said same plane such that the orientation of each of said planar serum applying surfaces may be independently adjusted when said planar serum applying surfaces come into contact with a serum bearing member.

8. A serum applicator according to claim 7, wherein each of said blood serum applicators comprises a penpoint having a generally planar serum applying surface and a penpoint support member.

9. A serum applicator according to claim 8, wherein said coupling means comprises:
  a slot formed in each of said penpoint support members; and
  a plurality of pairs of guide pins, each of said pairs of guide pins extending through said slot of a respective said penpoint support member, the width of each of said slots being slightly greater than the diameter of said guide pins extending therethrough.

* * * * *